United States Patent
Matallana-Kielmann

(10) Patent No.: US 8,590,405 B2
(45) Date of Patent: Nov. 26, 2013

(54) DEVICE FOR A TEST STRIP HOLDER, METHOD AND ARRANGEMENT

(76) Inventor: Michael Matallana-Kielmann, Moessingen (DE)

( * ) Notice: Subject to any disclaimer, the term of this patent is extended or adjusted under 35 U.S.C. 154(b) by 520 days.

(21) Appl. No.: 12/583,996

(22) Filed: Aug. 28, 2009

(65) Prior Publication Data

US 2009/0320623 A1     Dec. 31, 2009

Related U.S. Application Data

(63) Continuation of application No. PCT/DE2008/000459, filed on Mar. 25, 2008.

(30) Foreign Application Priority Data

Mar. 24, 2007  (DE) .......................... 10 2007 014 729

(51) Int. Cl.
*G01N 19/00* (2006.01)

(52) U.S. Cl.
USPC ........... 73/865.9; 73/428; 73/61.55; 73/61.58

(58) Field of Classification Search
USPC ........................... 73/865.9, 428, 61.55, 61.58
See application file for complete search history.

(56) References Cited

U.S. PATENT DOCUMENTS

| 6,277,646 | B1 | 8/2001 | Guirguis et al. |
| 6,464,939 | B1 | 10/2002 | Bachand et al. |
| 2003/0064526 | A1 | 4/2003 | Niedbala et al. |
| 2004/0184954 | A1* | 9/2004 | Guo et al. .................... 422/56 |
| 2006/0292034 | A1* | 12/2006 | Gould et al. .................. 422/58 |
| 2006/0292035 | A1* | 12/2006 | Gould et al. .................. 422/58 |

OTHER PUBLICATIONS

European Examination Report dated May 3, 2012 in European Application No. 12 00 0777 with English translation of the relevant parts.

* cited by examiner

*Primary Examiner* — Hezron E Williams
*Assistant Examiner* — Rodney T Frank
(74) *Attorney, Agent, or Firm* — Collard & Roe, P.C.

(57) ABSTRACT

For the simplified use of a test strip holder, a device having a holding or positioning device is provided, comprising a mixing chamber, a lid for closing the mixing chamber, and an obvious fluid opening for a fluid passage from the mixing chamber to the test strip holder. This allows for the test strip holder to be inserted into the device in a simple way and a sample can be prepared in the mixing chamber of the device. The device is provided with a mixing chamber that can be closed, wherein a reaction partner, for example a gold conjugate, can be dissolved in the sample for increasing the sensitivity of the test strip.

13 Claims, 1 Drawing Sheet

DEVICE FOR A TEST STRIP HOLDER, METHOD AND ARRANGEMENT

CROSS REFERENCE TO RELATED APPLICATIONS

Applicant claims priority under 35 U.S.C. §119 of German Application No. 10 2007 014 729.7 filed on Mar. 24, 2007. Applicant also claims priority and this application is a continuation under 35 U.S.C. §120 of International Application No. PCT/DE2008/000459 filed on Mar. 25, 2008, which claims priority under 35 U.S.C. §119 of German Application No. 10 2007 014 729.7 filed on Mar. 24, 2007. The international application under PCT article 21(2) was not published in English.

The invention relates to a device for a test strip holder, a method for the use of a test strip holder and an arrangement of such a device and a test strip holder inserted into the device.

Test strip holders are known for example for lateral flow immunoassay tests. These test strip holders comprise a test strip that at one of its ends is brought into contact with a sample and at the other end is in contact with a collecting pad in which sample material that has flowed through the test strip is collected. The test strip can comprise a nitrocellulose membrane on which test lines and control lines, which react with the sample and on which a reaction can be read, are arranged.

Such test strip holders facilitate the handling of a test strip and the loading of a sample onto the test strip as well as the reading of the results.

US 2004/0184954 A1 shows a generic test strip holder wherein using many parts a device is put together, with the help of which an access of a fluid to a test strip, which can be closed via a rotary motion, is achieved. This device has a complicated set-up, is expensive to produce and the use is cumbersome.

The invention is based on the object to further facilitate the use of such test strip holders.

This object is solved by a device for a test strip holder having the features of patent claim 1.

The mixing chamber that can be closed with a lid allows for a sample to be mixed with a further reactant prior to application to the measuring strip, optionally to be allowed to react and to be incubated. The fluid opening that can be opened allows for a sample prepared in such a manner to be allowed to flow to the measuring strip in a simple way.

Whereas until now the samples had to be laboriously pretreated for many tests, the device facilitates the preparation of the sample and the application of the sample onto the test strip. The holding or positioning device allows the positioning of the mixing chamber in the optimum position with respect to the test strip holder and preferably also holding it in this position. Thereby, a sample can be cleanly transferred from the mixing chamber onto the test strip.

Since the lid has two closing positions, in a first closing position the mixing chamber is sealed, and when the lid is moved into the second closing position the fluid opening is opened. This is achieved in a simple manner by a pin being arranged on the lid. Such a pin can open the fluid opening in the second closing position for example by pushing against a lid covering the fluid opening and opening the fluid opening at a predetermined breaking point.

The device can be so easily and cost-effectively produced that as injection molded plastic part it can be a disposable product, which after use is disposed together with the test strip and the test strip holder.

It is advantageous if the holding or positioning device is designed for the insertion of a test strip holder. The device can also be pressed onto the test strip holder and for example locked in place with it. However, a simple embodiment variant provides for the test strip holder to be inserted into the device and thereby to be optimally positioned with respect to the mixing chamber and held in this position.

This is achieved in a simple manner by the holding or positioning device comprising two sidewalls for positioning a test strip holder with respect to the fluid opening. These two sidewalls, which can be supplemented by additional sidewalls and stops, form a receiving unit for the test strip holder in order to transfer the sample without contamination cleanly from the mixing chamber onto the test strip holder.

An advantageous embodiment variant provides for the mixing chamber to comprise a reactant that can be transformed into a liquid phase. This reactant that is present in the mixing chamber for example as a solid material reacts only when it comes into contact with a liquid sample and is dissolved by moving the sample back and forth in the mixing chamber. Consequently, the reactant does not have to be metered first and added to the mixing chamber in the correct dosage since it is already present in the prefabricated mixing chamber.

In order to ensure optimal filling of the mixing chamber, it is proposed that the mixing chamber has a fill level mark. This can be a color mark or a special structure on the inside of the mixing chamber which specifies for the user how much sample volume needs to be filled into the mixing chamber.

A particularly clean mode of operation could be achieved by the mixing chamber comprising an upper opening section with a circumferential recess. Then, materials exiting the mixing chamber or sample hitting the upper edge collect in the circumferential recess so that contamination of the device is avoided when shaking the device.

Alternatively or cumulatively, the mixing chamber can also have a lowered plane surface at its upper opening section in order to avoid contamination.

A simple set-up results if the lid is arranged on the side of the mixing chamber opposite the fluid opening. For example, the lid can be arranged on the top side of the mixing chamber, whereas the fluid opening is arranged on the bottom side of the mixing chamber.

Losing the lid is avoided by the lid being connected to the mixing chamber. Preferably, the lid is connected to the mixing chamber by means of a strap. This strap is flexible and preferably elastic. Such a strap can position the lid with respect to the mixing chamber and thereby facilitate the process of putting the lid on the mixing chamber.

Good sealing of the lid is achieved by the lid having a circumferential edge that can be introduced into the mixing chamber.

In order to be able to simultaneously process several samples, which are the same or different, it is proposed that the device comprises a plurality of mixing chambers. The samples pretreated in the mixing chambers can subsequently be applied to different measuring strips. For this, either a test strip holder can comprise a plurality of test strips or the holding and positioning device is designed in such a way that it can jointly operate with a plurality of test strip holders.

When using the device with a plurality of test strips in particular, it is proposed that it comprises a wall that channels the fluid flow from the mixing chamber to each test strip when the fluid opening is open. Such a wall can be formed for example by a circumferential edge.

Handling of the test strip holders is also facilitated by a method for using a test strip holder in which a test strip is arranged in a test strip holder and the test strip holder is arranged on the device described above. Preferably, the test strip holder is inserted into the device.

Such a method allows for a sample to be fed into the mixing chamber and shaken. For this, a suitable reactant is preferably transformed from the solid phase into the liquid phase in the mixing chamber.

It is advantageous if the sample is incubated in the sample chamber for a period of time. Subsequently, it is provided for the bottom of the sample chamber to be pierced with a pin in the lid. This allows for the sample to flow from the device onto a test strip in the test strip holder.

At least one line is preferably present on the test strip. It is advantageous if a test line and a control line are arranged thereon. Such a line can be designed in the form of a point-shaped area; alternatively, a quadrangular area or an area in the form of a pad can also be provided.

The method allows for a result to be read after a time period suitable for the test.

Such a method is primarily suitable for test strip holders comprising a lateral flow immunoassay test.

Finally, the invention also relates to an arrangement of a device described previously and a test strip holder inserted into the device, this test strip holder comprising in particular a lateral flow immunoassay test.

In the following, the invention is explained in more detail by means of an exemplary embodiment.

In the figures.

Figure 1:
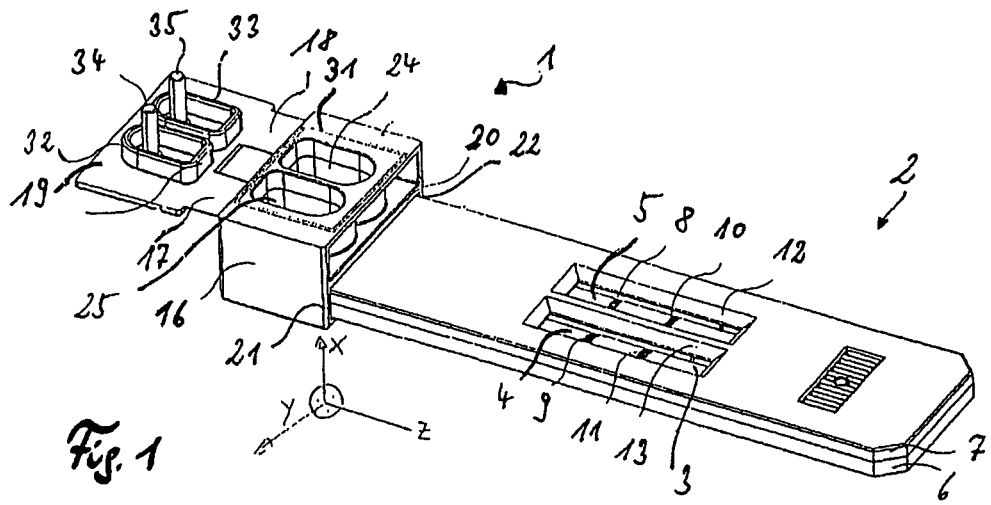
FIG. 1 shows a schematic perspective view of a device with a test strip holder.
Figure 2:
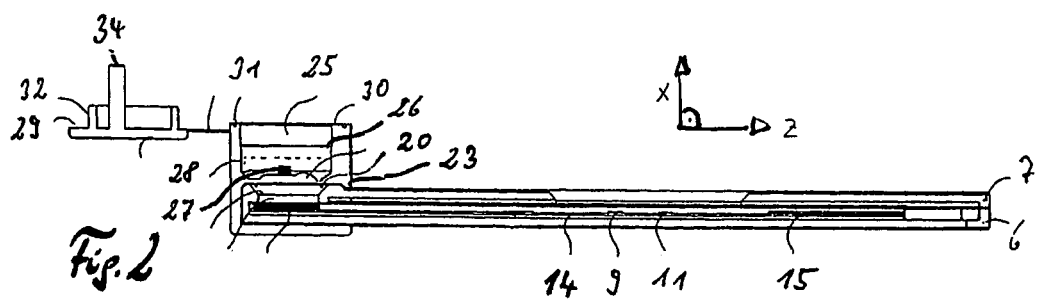
FIG. 2 shows a cut through the device shown in FIG. 1 with an open lid.

FIG. 1 shows the device 1 for a test strip holder 2 in which a lateral flow immunoassay test 3 with two test strips 4 and 5 is arranged.

Test strip holder 2 consists of two tray-shaped parts 6, 7 which are connected with one another and between which test strips 4, 5 are received. Test strips 4, 5 each have two test lines designed as test lines 8, 9 and control lines 10, 11. The result can be read through a reaction window 12, 13 formed in the upper tray-shaped part 7.

A nitrocellulose membrane 14 is disposed in test strip holder 2, which allows sample volumes to flow to test lines 8, 9 and control lines 10, 11. Afterwards, the sample collects in a collecting pad 15 at the end of the test strip holder.

Device 1 consists of a housing 16 on which a lid 19 is attached via two flexible straps 17 and 18. Housing 16 comprises in its lower section a holding and positioning device 20, which holds and positions test strip holder 2 by means of two sidewalls 21, 22. Hence, test strip holder 2 can be inserted into housing 16 like a drawer. An undercut 23 allows an attachment where test strip holder 2 is locked in place in housing 16.

Above holding and positioning device 20, two mixing chambers 24 and 25 are provided in the housing, into which a sample can be introduced when lid 19 is open. The sample is filled into the mixing chamber up to mark 26.

The sample covers a reactant 27 which initially is arranged in the solid phase at the bottom of the mixing chamber and is attached there. A reactant typical for a lateral flow immunoassay test is for example a gold conjugate, which can be transformed from the solid phase into a liquid phase in mixing chambers 24 and 25 by dissolving the reactant in the sample. Hereby, the sensitivity of the immunoassay test is increased.

Figure 3:
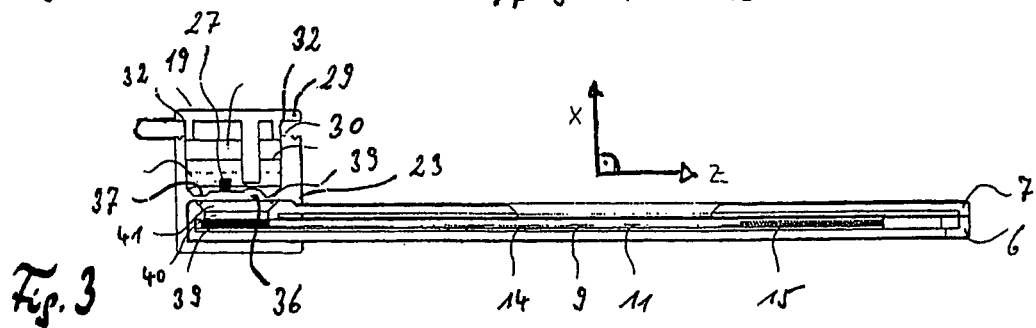
FIG. 3 shows a cut through the device shown in FIG. 1 with the lid in a first closing position.

Sample 28, which has been filled into mixing chamber 25, is kept in the mixing chamber by lid 19 shown in FIG. 3 in the put-on position. Hence, even when shaking device 1 to dissolve reactant 27, sample does not escape from the mixing chamber.

For example, should fluid collect at the upper opening section between the bottom side of the sample chamber lid 29 and the top side of the sample chamber 30 during filling, the purpose of a circumferential recess 31 is to hold this fluid so that it does not leave housing 16. Instead of a circumferential recess 31, a lowered plane surface that preferably opens towards the mixing chamber can also be provided.

Lid 19 comprises two circumferential edges 32, 33 that can be introduced into mixing chambers 24 and 25. In addition, lid 19 comprises a pin 34, 35 within each of the edges 32 and 33.

FIG. 3 shows how lid 19 seals the mixing chamber with edge 32 in a first closing position while a gap is still maintained between the bottom side of the sample chamber lid 29 and the top level of the sample chamber 30. In this position, pin 34 is above a stop 36 provided at the bottom of the mixing chamber 37.

Figure 4:
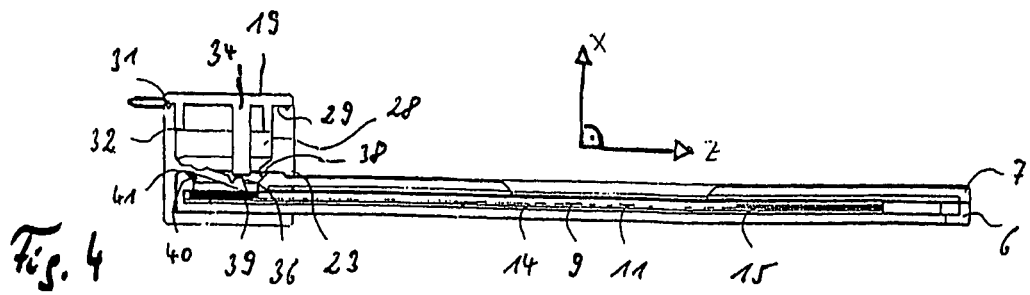
FIG. 4 shows a cut through the device shown in FIG. 1 with a lid in a second closing position.

Lid 19 can also be pressed-on more tightly—as shown in FIG. 4—so that edges 32 and 33 enter further into mixing chambers 24 and 25. In the process, pins 34 and 35, which are arranged on the lid, press onto chamber bottom 37 and there against stop 36. Hereby, a fluid opening 38 in the chamber bottom is opened by the breaking of predetermined breaking point 39, which allows for the passage of fluid from mixing chamber 25 to test strip holder 2.

After opening of fluid opening 38, sample 28 first flows onto sample pad 39 and from there via nitrocellulose membrane 14 to test and control strips 9 and 11.

To ensure that each sample reaches the correct test strip 4, 5 in particular in case of a plurality of fluid openings 38, a wall 40, 41 is provided that channels the fluid flow from mixing chamber 25 onto each test strip 4, 5 when fluid opening 38 is open.

The invention claimed is:

1. A device (1) for a test strip holder (2) with a holding and/or positioning device (20), a mixing chamber (24, 25) comprising a reactant (27) that can be transformed into a liquid phase, a lid (19) closing the mixing chamber (24, 25), a fluid opening (38) that can be opened for the passage of fluid from the mixing chamber (24, 25) to the test strip holder (2), and a strap (17, 18) that positions the lid (19) with respect to the mixing chamber (24, 25), wherein a pin (34, 35) is arranged on the lid (19); in a first closing position, the mixing chamber (24, 25) is sealed with the lid (19); and when the lid (19) is pressed on more tightly, the pin (34) opens the fluid opening (38) in a second closing position.

2. A device according to claim 1, wherein the holding and/or positioning device (20) is designed for insertion of a test strip holder (2).

3. A device according to claim 1, wherein the holding and/or positioning device (20) comprises two sidewalls (21, 22) for positioning a test strip holder (2) with respect to the fluid opening (38).

4. A device according to claim 1, wherein the lid (19) is arranged on the side of the mixing chamber (24, 25) opposite the fluid opening (38).

5. A device according to claim 1, wherein the lid (19) comprises a circumferential edge (32, 33) that can be introduced into the mixing chamber (24, 25).

6. A device according to claim 1, wherein it comprises a plurality of mixing chambers (24, 25).

7. A device according to claim 1, wherein a wall (40, 41) channels the fluid flow from the mixing chamber (25) to each of the test strips (4, 5) when the fluid opening (38) is open.

8. A method for using a test strip holder (2) in which a test strip holder is arranged on the device according to claim 1.

9. A method according to claim 8, wherein a sample is fed into the mixing chamber (25) and shaken.

10. A method according to claim 8, wherein a suitable reactant (27) is transformed from the solid phase into the liquid phase in the mixing chamber (24).

11. A method according to claim 8, wherein a sample is incubated in the mixing chamber (24).

12. A method according to claim 8, wherein the test strip holder comprises a lateral flow immunoassay test.

13. An arrangement of a device according to claim 1 and a test strip holder (2) inserted into the device.

* * * * *